United States Patent [19]
Sage et al.

[11] Patent Number: 6,025,532
[45] Date of Patent: Feb. 15, 2000

[54] PROCESS FOR THE MANUFACTURE OF HYDROFLUOROALKANES

[75] Inventors: Jean-Marc Sage, Oullins; Eric Lacroix, Amberieux D'Azergues; Philippe Bonnet; Eric Jorda, both of Lyons, all of France

[73] Assignee: Elf Atochem S.A., France

[21] Appl. No.: 09/098,749

[22] Filed: Jun. 17, 1998

[30] Foreign Application Priority Data

Jun. 18, 1997 [FR] France .................................. 97.07576

[51] Int. Cl.⁷ .................................................. C07C 17/00
[52] U.S. Cl. ............................................ 570/171; 570/159
[58] Field of Search ..................... 570/159, 171

[56] References Cited

U.S. PATENT DOCUMENTS

| | | |
|---|---|---|
| 3,009,966 | 11/1961 | Hauptschein et al. . |
| 3,154,592 | 10/1964 | Hauptschein et al. . |
| 3,222,406 | 12/1965 | Hauptschein et al. . |
| 4,258,225 | 3/1981 | Feiring . |
| 5,689,019 | 11/1997 | Aoyama et al. . |

FOREIGN PATENT DOCUMENTS

| | | |
|---|---|---|
| 36123 A1 B1 | 9/1981 | European Pat. Off. . |
| 349298 | 1/1990 | European Pat. Off. . |
| 456552 | 11/1991 | European Pat. Off. . |
| 506525 | 9/1992 | European Pat. Off. . |
| 773206 | 5/1997 | European Pat. Off. . |
| 539989 B1 | 6/1997 | European Pat. Off. . |
| 2716449 | 8/1995 | France . |
| 2731701 | 9/1996 | France . |
| 2049085 | 11/1995 | Russian Federation . |
| 91/05752 | 5/1991 | WIPO . |
| 92/02476 | 2/1992 | WIPO . |
| 96/02483 | 2/1996 | WIPO . |

*Primary Examiner*—Elli Peselev

[57] ABSTRACT

In order to manufacture pentafluoroethane (F125) and/or 1,1,1,2,3,3,3-haptafluoropropane (F227ea), a trifluoromethane gas stream is subjected to pyrolysis and then the mixture of gases which result from this pyrolysis is brought into contact with a fluorination catalyst.

29 Claims, No Drawings

PROCESS FOR THE MANUFACTURE OF HYDROFLUOROALKANES

FIELD OF THE INVENTION

The present invention relates to the field of hydrofluoroalkanes, commonly known as HFCs or HFAs, and has more particularly as subject-matter the manufacture of pentafluoroethane (F125) and of 1,1,1,2,3,3,3-heptafluoropropane (F227ea) from trifluoromnethane, known under the designation F23.

BACKGROUND OF THE INVENTION

Interest in hydrofluoroalkanes has grown since chlorofluoroalkanes (CFCs) have been suspected as contributing to the weakening of the stratospheric ozone layer.

CFCs, such as fluorotrichloromethane (CFC 11), dichlorodifluoromethane (CFC 12), 1,1,2-trichloro-1,2,2-trifluoroethane (CFC 113) and chloropentafluoroethane (CFC 115), have for this reason been banned in ail industrialized countries and have been replaced by hydrofluoroalkanes, such as 1,1,1,2-tetrafloroethane (F134a), difluoromethane (F32), pentafluoroethane (F125), 1,1,1,2,3,3,3-heptafluoropropane (F227ea), 1,1,1,3,3-pentafluoropropane (F245fa) and 1,1,1,2,2-pentafluorobutane (F365mfc), and by hydrochlorofluoroalkanes (HCFC), such as chlorodifluoromethane (F22), 1,1-dichloro-1-fluoroethane (F141b) and 1-chloro-1,1-difluoroethane (F142b). Although less harmful than CFCs to the ozone layer, HCFCs ire, however, destined to gradually disappear. It is therefore necessary to be able to manufacture products of HFC type in order to replace CFCs and HCFCs.

The majority of processes currently known for the synthesis of HFCs are based on the catalytic fluorination of chlorinated compounds using hydrogen fluoride or on the hydrogenolysis of a chlorofluorinated compound or on the pyrolysis of an HCFC in the presence of HFCs. It is obvious that all these processes, which involve a chlorinated product and which coproduce hydrochloric acid, give, as impurities, chlorinated products of HCFC or CFC type which are not very desirable because of their effects on the ozone layer. The content of chlorinated Impurities of CFC or HCFC type in the HFCs thus manufactured must be as low as possible and is thus an important factor to be taken into consideration.

Due to the various applications of these products (refrigeration, air conditioning, expansion of foams, solvent or extinguishing of fires), it may prove necessary to have available several HFCs possessing different physical and chemical properties or mixtures of HFCs more specifically satisfactory for certain applications.

It would be particularly advantageous in this field to have available a process making possible the manufacture of several HFCs with different physical properties from the same starting material without resulting in the formation of chlorinated byproducts and impurities of HCFC or CFC type or of hydrochloric acid, in particular for manufacturing pentafluoroethane (F125) and 1,1,1,2,3,3,3-heptafluoropropane (F227ea).

Mention may be made, among the numerous processes for the synthesis of F125 from a chlorinated or chlorofluorinated derivative, of:

those relating to the fluorination of 1,1,1-trifluoro-2,2-dichloroethane (F123) by hydrogen fluoride in the gas phase in the presence of a catalyst containing chromium deposited on a charcoal support (Patent EP 456,552) or in the presence of a catalyst containing chromium on a support of fluorinated alumina type (Patent EP 349,298), the disproportionation of an HCFC derivative, such as F124, the passage of which over a catalyst of chromium oxide type results, at the outlet, in a mixture of F125 and F123 (Patent Application WO 9202476), the hydrogenolysis of F115 (Application WO 9105752 and Patent EP 0,506,525), a degree of conversion of F115 of greater than 99% requiring forcing conditions which result in the formation of significant amounts of F143a ($CF_3$—$CH_3$).

These processes, involving chlorinated derivatives of the HCFC or CFC type, generally involve a thorough purification of the F125 obtained, one of the major problems being the presence in the F125 of F115, which is difficult to separate by simple distillation and which has to be removed by more complex techniques, as described in Patent ER 2,716,449.

F125 can also be obtained by fluorination of tetrafluoroethyline in the liquid phase (Patent U.S. Pat. No. 4,258,225) or gaseous phase (Patent EP 0,036,123) in the presence of catalysts, but these processes require the isolation or the storage of $C_2F_4$, which constitutes a major handicap because of the dangers of explosion or off polymerization inherent in this product. According to Patent RU 2,049,085, the fluorination of $C_2F_4$ as a mixture with F124 can be carried out in the gas phase with a catalyst based on chromium on an aluminium oxide: $C_2F_4$ and F124 can result from the pyrolysis of F22 ($CHClF_2$) but the F125 thus obtained is contaminated by HCFCs, such as F114 and F115, which greatly reduces the advantage of such a process.

Patent ER 2,731,701 describes a process for the synthesis of F125 from a mixture of F23 and F22. Although this process makes it possible to produce other HFCs than F125, it requires the use of a chlorinated starting material, F22; moreover, the presence of HCl formed by the reaction is also not very desirable, because of the problems of corrosion and of the chlorinated byproducts which it can generate in the reaction mixture.

Patent U.S. Pat. No. 3,009,966 describes a process for the manufacture of perfluorinated olefins comprising a stage of pyrolysis of F23 and indicates that very small amounts of F125 and F227ea are also formed.

Mention may be made, among the various processes for the synthesis of F227ea, of the hydrogenolysis of 2-chloroheptafluoropropane over metal catalysts (Patent EP 539,989) and the fluorination by HF of perfluoropropene in the presence of an antimony-comprising catalyst (Patent Application WO 9602483).

DESCRIPTION OF THE INVENTION

It has flow been found that, starting with trifluoromethane (F23), it is possible to prepare pentafluoroethane (F125), 1,1,1,2,3,3,3-haptafluoropropane (F227ea) or a mixture of these compounds, with good yields, by a process which does not involve any chlorinated product or byproduct and which thus provides F125and F227ea which are devoid of impurities of CFC or HCFC type usually present in the products obtained by processes based on the use or chlorinated starting materials. In addition, this process makes it possible to coproduce hydrofluoric acid which is devoid of any trace of hydrochloric acid.

The subject-matter of the invention is thus a process for the manufacture of pentafluoroethane F125, and/or of 1,1,1,2,3,3,3-heptafluoropropane (F227ea), characterized in that it comprises:

(a) a stage which consists in subjecting, in the gas phase, a stream of trifluoromethane (F23) to pyrolysis at a temperature of greater than 700° C., and (b) a stage which consists in bringing the mixture of gases which result from the pyrolysis stage into contact with a fluorination catalyst.

In stage (a) of the process according to the invention, the pyrolysis of F23 results in the formation of tetrafluoroethylene and/or of perfluoropropene and in the coproduction of hydrogen fluoride.

In stage (b), carried out in the presence of a fluorination catalyst, a portion of the HF coproducer in stage (a) is added to the tetrafluoroethylene and/or the perfluoropropene to form F125 and/or F227ea, As shown in the following reaction scheme:

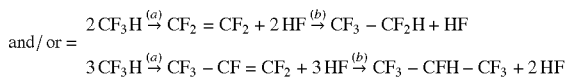

the HF formed during stage (a) is only partially consumed during stage (b). The excess can thus be easily recovered in order to be exploited in other manufacturing operations. Moreover, the absence of hydrochloric acid in the reaction mixture prevents the corrosion problems induced by the presence of hydrochloric acid at high temperature.

Stage (a) can be carried out under vacuum or under pressure. The pyrolysis can thus be carried out under an absolute pressure ranging from 10 mbar up to 10 bar, an excessively high pressure resulting in significant losses in selectivity with respect to product and an excessively low pressure decreasing the productivity of the process. The choice of this pressure is also related to the desired orientation towards the intermediate production of $C_2F_4$ or of $C_3F_6$ during the first stage or else the final production of F125 or of F227ea on conclusion of the second stage. A low pressure is favourable to formation of $C_2F_4$ and thus of F125, whereas a higher pressure promotes the formation of $C_3F_6$ and thus of F227ea. The operation is preferably carried out under a pressure of between 50 mbar and 2 bar, a pressure value equal to atmospheric pressure being moreover preferred.

The pyrolysis stage (a) is carried out at a temperature of greater than 700° C. but the exact choice of the pyrolysis temperature depends on the contact time chosen and on the products desired at the outlet of the process; the upper limit of this temperature is generally set by technological constraints. This pyrolysis temperature is usually between 700 and 1200° C.; it is preferably chosen between 900 and 1100° C. and, more preferably still, between 930 and 1050° C.

The contact time as shown hereinbelow is defined by the ratio of the volume of the heated region to the gas flow rate, expressed as volume per unit of time, this gas flow rate being corrected for the pressure and temperature conditions of the reaction stage by applying the relationship for perfect gases. The choice of the contact time during stage (a) is obviously related to the temperature and pressure conditions involved. It is generally between 0.1 millisecond and 2 seconds, preferably between 5 milliseconds and 0.1 second and, more preferably still, between 5 and 50 milliseconds. The lower limit of this contact time is in fact dictated by technological limits relating to the temperatures and the gas flow rates to be employed.

The reactor in which the pyrolysis stage (a) is carried out is preferably a reactor of empty tubular type but it is also possible to use a reactor filled with an inert packing, in order to increase the exchange surface areas. Although it is possible to introduce a bulk or supported catalyst into the reactor, the pyrolysis stage does not normally require a catalyst and is preferably carried out in the absence of catalyst.

The reactor can be made of various materials which withstand the temperature and pressure conditions and which are resistant to corrosion. It is possible, for this, to use reactors coated internally with, for example, platinum; however, without limiting the scope of the invention, preference is given to materials such as Inconel, nick/al or Hastelloy.

The F23 can be introduced, into the pyrolysis reactor, pure or as a mixture with a recyclate of different product's formed during the process. Without limiting the scope of the invention, it may be indicated that these products and byproducts can be F125, F227ea, perfluorocyclobutane (c-$C_4F_8$), tetrafluoroethylene, perfluoropropene, hexafluoroethane (F116) or hydrofluoric acid. An inert diluent gas, such as nitrogen, can also be introduced.

The gases resulting from the pyrolysis stage (a), containing, as main products, unreacted F23, HF and a mixture of perfluoropropene and of tetrafluoroethylene which, according to the orientation chosen, can contain mostly one or other of these two products, are conveyed to a reactor containing a fluorination catalyst which operates at a temperature below 500° C.

The crude mixture of the gases which result from the pyrolysis sage (a) is preferably conveyed directly to the fluorination reactor but it can also be the subject of an intermediate or buffer storage, in order to make it easier to carry out the process. Recycling products and in particular hydrogen fluoride can be added to the mixture of the gases originating from the pyrolysis stage. In order to stabilize the perfluorinated olefins and to prevent their polymerization, it is also possible to add, to the flow feeding the fluorination reactor, one or more stabilizing agents, such as, for example, terpenes, such as limonene or the mixture known under the name of Dipsol®, phenols, amines and certain aromatic derivatives, such as toluene or alpha-methylstyrene.

The fluorination reaction can be carried out in the gas phase or liquid phase.

When the reaction is carried out in the gas phase, use is generally made of a catalyst based on metal fluorides and/or oxides, such as those of chromium, nickel, zinc, magnesium, calcium or iron. The catalyst used can be bulk in nature or supported on a substrate which can be an aluminium fluoride, a charcoal or any other support which is resistant to the presence of hydrogen fluoride. Catalysts based on chromium give good results and one of the preferred catalysts is composed of a catalyst comprising chromium deposited on a, support based on fluorinated alumina.

The temperature of the fluorination stage, carried out in the gas phase, can be between 200 and 500° C.; however, it is preferable to operate at a temperature of between 200 and 400° C. and more particularly between 250 and 350° C. In the gas phase, the pressure of the fluorination stage can vary between 10 mbar and 20 bar; it is advantageously between 100 mbar and 5 bar and more advantageously equal to atmospheric pressure. It is obvious that, from a technological viewpoint, it is advantageous to choose similar pressures for the two stages of the process.

The contact time during this fluorination stage in the gas phase is between 0.1 and 120 seconds, the operation is preferably carried out with a contact time of between 1 and 30 seconds.

It is also possible to carry out the fluorination stage (b) in the liquid phase under pressure. The reaction can then be carried out in the presence or absence of a solvent, in particular in so-called HF medium, in which hydrofluoric acid is used as solvent medium.

Mention may be made, without implied limitation, as catalyst for the fluorination in the liquid phase of the usual catalysts, which are antimony, titanium, tin, tantalum or niobium derivatives. The fluorination temperature in the liquid phase can vary between 20 and 150° C.

At the outlet of the fluorination stage, the gases, mainly containing F23, hydrofluoric acid, F125 and/or F227ea, are separated. It is preferable to operate under conditions which do not provide residual olefins $C_2F_4$ or $C_3F_6$; however, if these olefins are still present at thee outlet of the fluorination stage, they can either be recycled in the process or recovered for other uses.

It is possible to wash the gases at the outlet with an aqueous solution, in order to remove the hydrofluoric acid, and then to distill the gases, in order to recover the F125 and/or F227ea formed; the F23 is generally returned to the beginning of the reaction, as well as all or part of the other unconverted intermediates or byproducts. It is also possible to distill the crude gases resulting from this second stage, in order to recover the HF in a form which can be more readily reused industrially or to recover the hydrogen fluoride by washing with sulphuric acid.

EXAMPLES

The following examples illustrate the invention without limiting it.

EXAMPLE 1

(a) Preparation of the Fluorination Catalyst p 1 litre of an alumina impregnated to 6% with chromium by means of a solution of chromium oxide $CrO_3$ in methanol is charged to a 1.5 litre Inconel reactor with an internal diameter of 8 cm heated by means of a fluidized sand bath device.

The alumina employed is a commercial alumina exhibiting the following characteristics:

| - form: | 1–2 mm beads |
| --- | --- |
| - BET specific surface: | 223 m²/g |
| - pore volume: | 1.2 cm³/g (for pore radii of between 4 nm and 63 μm). |

The catalyst is dried overnight at 200° C. while flushing with nitrogen and then, at this temperature and in the presence of nitrogen, 240 g of hydrogen fluoride are introduced at a flow rate of 18 g/h. The temperature is subsequently brought to 350° C. and the introduction of HF is continued at the same flow rate for a further 12 hours. The fluorination catalyst used in the second stage of the process is thus obtained.

(b) Pyrolysis of Trifluoromethane

Trifluoromethane (F23), preheated to 170° C., is introduced into a reactor consisting of an empty nickel tube with a length of approximately 50 cm, an internal diameter of 4 mm and an external diameter of 6 mm. This tube is heated by a furnace; the length actually heated to a temperature in the region of the set temperature (temperature of between the set temperature and this same temperature decreased by 20° C.) was evaluated experimentally at 20 cm by introducing a temperature probe into this tube and by passing nitrogen, this temperature probe being removed during the tests. This length is taken into consideration in evaluating the contact time during this first stage. The set temperature (T1) for this example is 1000° C. and the contact time (ct1) is 32 milliseconds.

(c) Fluorination of the Pyrolygis Product

The reactor in which this second stage of the process is carried out is the reactor described in paragraph (a) and is charged with the catalyst prepared in paragraph (a). The gases resulting from the pyrolysis stage described in paragraph (b) are directly conveyed to this fluorination reactor. The temperature of this second stage (T2) is set at 300° C.; the pressure is equal to atmospheric pressure and the contact time (ct2), calculated with respect to the volume of catalyst, is 29 seconds. At the outlet of the second reactor, the gases are washed with water and then dried over calcium chloride.

The results obtained are reported in the following table.

EXAMPLE 2

The operation is carried out as in Example 1, but by changing the flow rate of F23 admitted, that is to say by modifying the contact times of the two stages of the process. The results are reported in the following table.

EXAMPLE 3

The operation is carried out in a way similar to the preceding examples but by using a pyrolysis reactor (first stage) with an internal diameter of 2 mm and an external diameter of 4 mm, the heating region being equal to 20 cm. Moreover, the operation is carried out with a lower volume of catalyst during the second stage, in order to have a contact time of 15 seconds. The results obtained are reported in the following table.

| Example | T1 °C. | ct1 seconds | T2 °C. | ct2 seconds | F23 | F125 | F227ea | c-$C_4F_8$ | F116 | $C_4F_9H$ | Others |
| --- | --- | --- | --- | --- | --- | --- | --- | --- | --- | --- | --- |
| | | | | | \multicolumn{7}{c}{Molar % (VPC analysis)} | | | | |
| 1 | 1000 | 0.032 | 300 | 29 | 78.4 | 15.1 | 4.04 | 0.14 | 1.15 | 0.16 | 1.01 |
| 2 | 1000 | 0.025 | 300 | 22 | 84.8 | 11.4 | 2.0 | 0.10 | 0.97 | 0.08 | 0.65 |
| 3 | 1000 | 0.010 | 300 | 15 | 86.2 | 12.0 | 0.99 | 0.05 | 0.32 | 0.02 | 0.42 |

EXAMPLE 4

The operation was carried off under the same conditions as Ln Example 3. After functioning for more than 100 hours, no sign of deactivation of the fluorination catalyst was recorded and the distribution of the products remained unchanged.

EXAMPLE 5

The equipment used is composed of a 11 316L stainless steel jacketed autoclave surmounted by a simple condenser, also jacketed, and by a pressure control valve.

502 g of HF (25.1 mol) and 71.7 g of $TaCl_5$ (0.2 mol) are successively charged to this autoclave, which has been immersed in liquid nitrogen. The temperature of the autoclave is then brought back to ambient temperature. The autoclave is then immersed in an oil bath, so as to obtain a temperature of approximately 100° C. in the reaction mixture, whereas the temperature at the top of the condenser is maintained at 20° C. and the assembly is adjusted to a pressure of 10 bar.

When the temperature of 100° C. is reached, $C_2F_4$ is supplied in then gas phase at a flow rate of 14.9 g/h (0.3 mol/h). The most volatile products, discharged continuously at the top of the condenser, pass into a water sparger and then into a drier, before being collected in at stainless steel receptacle cooled with liquid nitrogen.

After reacting for 2 h, the autoclave is cooled by circulation of water in the oil bath. After returning to ambient temperature, the autoclave is degassed and the reaction products are washed, dried and collected as above. The gas phases and the liquid phases thus collected are analysed, as well as the liquid phase which may possibly remain in the autoclave after the degassing.

The conversion (expressed with respect to 100 mol of $C_2F_4$ introduced) amounts to 12.9% with a selectivity (expressed with respect to the number of moles of $C_2F_4$ consumed by the reaction) for F125 of 99.9%.

EXAMPLE 6

Example 5 is repeated, 482 g of HF (24.1 mol) and 50.6 g of $NbCl_5$ (0.19 mol) being successively charged to the autoclave, which has been immersed in liquid nitrogen, and $C_2F_4$ being supplied in the gas phase with a flow rate of 15.1 g/h (0.3 mol).

After reacting for 2 h, analysis of the gas and liquid phases shows that the conversion of the $C_2F_4$ introduced amounts to 11% with a selectivity for F125 of 99.9%.

Examples 5 and 6 show that the mixture of gases resulting from the pyrolysis reaction of F23 according to stage (a) of the process according to the invention can be subjected to a catalysed fluorination reaction in the liquid phase to give F125.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the manufacture of pentafluoroethane and/or of 1,1,1,2,3,3,3-heptafluoropropane, comprising:
   a) a stage which consists in subjecting, in the gas phase, a stream of trifluoromethane to pyrolysis at a temperature of greater than 700° C. and
   b) a stage which consists in bringing the mixture of gases which results from the pyrolysis stage into contact with a fluorination catalyst, wherein said process does not involve the production of any chlorinated product or byproduct.

2. Process according to claim 1, wherein the pyrolysis stage is carried out at a temperature ranging from 700° C. to 1200° C.

3. Process according to claim 1, wherein the pyrolysis stage is carried out under a pressure ranging from 10 mbar to 10 bar.

4. Process according to claim 2, wherein the contact time is between 0.1 millisecond and 2 seconds.

5. Process according to claim 1, wherein the pyrolysis reactor is an empty tubular reactor.

6. Process according to claim 1, wherein the trifluoromethane supplied to the pyrolysis reactor is pure, diluted with an inert gas and/or mixed with a recycled products.

7. Process according to claim 6, wherein the recycled products comprise pentafluoroethane, 1,1,1,2,3,3,3-heptafluoropropane, perfluorocyclobutane, tetrafluoroethylene, perfluoropropene, hexafluoroethane and/or hydrogen fluoride.

8. Process according to claim 1, wherein the fluorination stage is carried out in the gas phase at a temperature ranging form 20° C. to 500° C.

9. Process according to claim 8, wherein the fluorination stage is carried out under a pressure ranging form 10 mbar to 20 bar.

10. Process according to claim 8, wherein the contact time is between 0.1 and 120 seconds.

11. Process according to claim 8, wherein the fluorination catalyst is based on chromium.

12. Process according to claim 1, wherein the fluorination stage is carried out in the liquid phase under pressure.

13. Process according to claim 12, wherein the fluorination catalyst is based on antimony, on titanium or on tin.

14. Process according to claim 12, wherein the temperature is between 20° C. and 150° C.

15. Process according to claim 12, wherein the fluorination is carried out in solvent medium.

16. Process according to claim 8, wherein byproducts of the process are added to the gas flow resulting from the pyrolysis stage.

17. Process according to claim 8, wherein a stabilizing agent is added to the gas flow resulting from the pyrolysis stage.

18. Process according to claim 2, wherein the temperature is between 900° C. and 1100° C.

19. Process according to claim 2, wherein the temperature is between 950° C. and 1050° C.

20. Process according to claim 3, wherein the pressure is between 50 mbar and 2 bar.

21. Process according to claim 3, wherein the pressure is atmospheric.

22. Process according to claim 4, wherein the contact time is between 5 millisecond and 0.1 second.

23. Process according to claim 4, wherein the contact time is between 5 and 50 millisecond.

24. Process according to claim 8, wherein the temperature is between 200° C. and 350° C.

25. Process according to claim 8, wherein the temperature is between 250° C. and 350° C.

26. Process according to claim 9, wherein the pressure is between 100 mbar and 5 bar.

27. Process according to claim 9, wherein the pressure is atmospheric.

28. Process according to claim 15, wherein the contact time is between 1 and 30 seconds.

29. Process according to claim 15, wherein the solvent medium is HF.

* * * * *